United States Patent
Rath et al.

(10) Patent No.: US 9,018,437 B2
(45) Date of Patent: Apr. 28, 2015

(54) TRANSGENIC MOUSE EXPRESSING HUMAN APO(A) AND HUMAN APO(B-100) WITH DISABLED VITAMIN C GENE PRODUCES HUMAN LP(A)

(71) Applicants: Matthias W Rath, Aptos, CA (US); Aleksandra Niedzwiecki, Aptos, CA (US); John Chang-Eun Cha, San Mateo, CA (US)

(72) Inventors: Matthias W Rath, Aptos, CA (US); Aleksandra Niedzwiecki, Aptos, CA (US); John Chang-Eun Cha, San Mateo, CA (US)

(73) Assignee: Matthias W. Rath, Aptos, CA (US)

( * ) Notice: Subject to any disclaimer, the term of this patent is extended or adjusted under 35 U.S.C. 154(b) by 0 days.

(21) Appl. No.: 14/025,532

(22) Filed: Sep. 12, 2013

(65) Prior Publication Data

US 2015/0074837 A1     Mar. 12, 2015

(51) Int. Cl.

| | |
|---|---|
| *A01K 67/033* | (2006.01) |
| *A01K 67/027* | (2006.01) |
| *C12N 15/00* | (2006.01) |
| *G01N 33/00* | (2006.01) |
| *A61K 49/00* | (2006.01) |
| *G01N 33/92* | (2006.01) |
| *C12N 15/85* | (2006.01) |
| *C12N 15/90* | (2006.01) |
| *C07K 14/775* | (2006.01) |

(52) U.S. Cl.
CPC ......... *A61K 49/0008* (2013.01); *C12N 15/8509* (2013.01); *A01K 2217/00* (2013.01); *A01K 2267/0362* (2013.01); *A01K 67/0275* (2013.01); *A01K 2267/0337* (2013.01); *A01K 2217/05* (2013.01); *A01K 67/0278* (2013.01); *C12N 15/90* (2013.01); *G01N 33/92* (2013.01); *A01K 2207/15* (2013.01); *C07K 14/775* (2013.01); *A01K 2227/105* (2013.01); *A01K 2267/03* (2013.01)

(58) Field of Classification Search
CPC .. C12N 15/8509; C12N 15/90; C07K 14/775; A01K 2217/05; A01K 2227/105; A01K 67/0275; A01K 2207/15; A01K 2217/00; A01K 2267/03; A01K 2267/0337; A01K 67/0278; A01K 2267/0362; G01N 33/92
See application file for complete search history.

(56) References Cited

U.S. PATENT DOCUMENTS 6,512,161 B1   1/2003 Rouy et al.

OTHER PUBLICATIONS

Brevini et al., No shortcuts to pig embryonic stem cells, Theriogenology, 2010, vol. 74, pp. 544-550.*
Paris et al., Equine embryos and embryonic stem cells: Defining reliable markers of pluripotency. Theriogenology, 2010, vol. 74, pp. 516-524.*
Munoz et al. Conventional pluripotency markers are unspecific for bovine embryonic-derived cell-lines. Theriogenology, 2008, vol. 69, pp. 1159-1164.*
Kare Ber, A New Serum Type System in Man—The Lp System, Acta Path. 59. 3, 369-382.
Zenker G., et al., Lipoprotein(a) as a strong indicator for cerebrovascular disease, Stroke. 1986;17:942-945.
John W. McLean et. al., cDNA Sequence of Human Apolipoprotein (A) is Homologous to Plasminogen, Nature, vol. 300, 12, Nov. 1987.
Emile Zuckerkandl et. al., A comparison of animal hemoglobins by tryptic peptide pattern analysis, Biochemistry, vol. 46, 1960, 1349-1360.
Nobuyo Maeda et al., Aortic wall damage in mice unable to synthesize ascorbic acid, PNAS, Jan. 18, 2000, vol. 97, No. 2, 841-846.
M Rath et. al., Detection and quantification of lipoprotein(a) in the arterial wall of 107 coronary bypass patients, Arterioscler Thromb Vasc Biol. 1989;9:579-592.
Robert Clark et. al., Genetic Variants Associated with Lp(a) Lipoprotein Level and Coronary Disease, N Engl J Med 2009;361:2518-28.
George G. Rhoads et. al., Lp(a) Lipoprotein as a Risk Factor for Myocardial Infarction, JAMA 1986;256:2540-2544.
Emile Zuckerkandl et.al., Molecules as Documents of Evolutionary History, J. Theoret. Biol. (1965) 8, 357-366.
I.B. Chatterjee, Evolution and the Biosynthesis of Ascorbic Acid, Science, vol. 182, 1271-1272.

* cited by examiner

*Primary Examiner* — Deborah Crouch
(74) *Attorney, Agent, or Firm* — Geeta Kadambi; Riddhi IP LLC

(57) ABSTRACT

The invention discloses novel model of transgenic mammal, a method of crossbreeding transgenic mammal and the use of the transgenic mammal for assessing prevention and/or treatment methods for cardiovascular and other diseases related to lipoprotein(a). The transgenic mammal expresses human apolipoprotein (a) (apo(a)) and human apolipoprotein B-100 (apo B-100) genes and produces human lipoprotein (a), apo (a) and apo B-100 and produces no vitamin C. This novel dual transgenic mammal is the ideal model for testing pharmaceutical compounds for efficacy and usefulness in the prevention and/or treatment of human diseases.

9 Claims, 8 Drawing Sheets

TRANSGENIC MOUSE EXPRESSING HUMAN APO(A) AND HUMAN APO(B-100) WITH DISABLED VITAMIN C GENE PRODUCES HUMAN LP(A)

FIELD OF TECHNOLOGY

This disclosure relates generally to a transgenic mouse that has been genetically altered to express human lipoprotein (a) and a disabled gene for the expression of Vitamin C. More specifically the two defining human proteins of lipoprotein (a), apolipoprotein (a) and apolipoprotein B-100 gene may be expressed either individually or in combination without the expression of Vitamin C gene. This application contains sequence listing that has been submitted as an ASCII file named RIPLLC018017US1sequence_ST25, the date of creation Sep. 12, 2013, and the size of the ASCII text file in bytes is 2 kb. The dual transgenic mouse embryo referred to as Rath M Human Lipoprotein(a); Gulo(−/−) has the Jackson Stock #912329, having been deposited in The Jackson Laboratory on Apr. 8, 2013.

BACKGROUND OF THE INVENTION

Cardiovascular disease is responsible for half of the deaths in the industrial world. Over the past decades a new risk factor for this disease has emerged, lipoprotein (a) (Lp (a)). Lp (a) is has been shown to be an independent risk factor for myocardial infarctions, (Rhoads G G et. al., 1986, Clarke et al, 2009) cerebrovascular disease (Zenker G et. al., 1986) and other forms of cardiovascular disease. Furthermore, Lp(a) has been identified as a significant component of human atherosclerotic plaques (Rath M et. al., 1989). Aside from Niacin, there is currently no accepted effective treatment available in clinical cardiology to lower Lp(a) plasma levels or to prevent its deposition inside the vascular wall.

Lp(a) was discovered by Kare Berg in 1963 (Berg, K et. al., 1963). It is composed of a low-density-lipoprotein molecule (LDL) and apolipoprotein (a) (apo(a)), a glycoprotein attached to the structural protein of LDL, apolipoprotein B-100 (apo B), via disulfide bonds. The cDNA of apo(a) shows a strong homology with plasminogen containing multiple repeats of plasminogen kringle IV. Due to this homology apo(a) binds to fibrinogen/fibrin and attenuates fibrinolysis (McLean, J W et. al. 1987).

Lp(a) is primarily found in humans and subhuman primates and the appearance of the apo(a) gene was dated to about 40 million years ago, about the time of the divergence of the Old World and New World monkeys (McLean, et al. Nature, 1987). This was also the time point during evolution when the ancestor of man lost the ability for endogenous ascorbate synthesis due to a mutation in the gene encoding for gulonolactone oxidase (GULO), an essential enzyme for the conversion of glucose to ascorbate (vitamin C) (Chatterjee I B, 1973, Nikishimi M et al., 1991).

The significance of ascorbate deficiency in initiating the process of atherogenesis has recently been documented in mouse unable to express the gene for L-gulonolactone oxidase (GULO −/−) (Maeda N et. al., 2000).

Roy et. al. (2003, U.S. Pat. No. 6,512,161) discusses several failed attempts to create animal models for expressing specifically Lp(a) in models such as rats, mouse and guinea pigs and state that they don't always represent human metabolism and human-related diseases. In their study they invented a rabbit model expressing human apo (a) and human apo B-100 genes. However, the transgenic rabbit developed by Roy et. al. (2003) also does not mimic the human physiology with respect to another key metabolic aspect: unlike humans, rabbits are able to produce their own Vitamin C.

There exists a need for a dual transgenic mammal model displaying these unique genetic features in order to develop new preventive and therapeutic approaches related to them.

SUMMARY

The current application discloses a method of making and using a dual transgenic mammal (mouse, rat and other mammalian species) that possesses the genes for human apo (a) and/or apo B-100 and produces human (Lp(a) while, at the same time, being unable to produce vitamin C. In one embodiment, a third strain of transgenic mammal was obtained by crossbreeding the first knockout strain mammal and second strain of transgenic mammal (may be a mouse or other animals) expressing a set of genes that are human in nature, wherein the first strain is a knockout mammal possessing a non-functional L-gulonolactone oxidase (GULO) (GULO−/−) and hence produces no Vitamin C, wherein the second strain of mice expresses human apo (a) gene (apo (a)+) and produces apolipoprotein (a)(apo (a)), wherein the third strain of transgenic mice possesses non-functional L-gulonolactone oxidase (GULO−/−) gene and a functional human apo (a) gene (apo (a)+). Hence this third strain of mammal will not produce vitamin C but will produce human apo (a).

In another embodiment, a fifth strain of transgenic mammal was made by crossbreeding the first knockout strain mammal possessing non-functional L-gulonolactone oxidase (GULO−/−) gene and the fourth strain expressing human apo B-100 gene (apo (B-100)+), wherein the fifth strain of mammal possesses non-functional L-gulonolactone oxidase (GULO−/−) gene and a functional human apo B-100 gene (apo (B-100)+). Hence the fifth strain of transgenic mammal will not produce vitamin C and will produce human apolipoprotein B-100.

In another embodiment, third strain and fifth strain of transgenic mammal were crossbred to obtain a novel dual transgenic mammal (may be a mouse for example) that had a knockout GULO gene (GULO−/−), a functional human apo B-100 gene (apo(B-100)+) and a functional human apo (a) gene (apo (a)+). The novel dual transgenic mammal will hence, produce apolipoprotein (a)(apo (a)) and/or apolipoprotein B-100 (apo B-100) as well as the complete lipoprotein (a) particle (Lp(a) and will not produce vitamin C. This novel double transgenic mammal model resembles the human system with respect to the inability of endogenous ascorbate synthesis and, congruently, the expression of apo(a), apo (B-100) as well as the complete lipoprotein(a) particle (Lp (a)). In the instant disclosure a mouse model is used but other mammals may be used and crossbreeding, insertion of genes or deletion of genes may be done to produce these dual transgenic mammals to express or suppress human genes in any combination.

In one embodiment, a mammal, a mouse whose genome lacks the ability for endogenous ascorbate synthesis and—simultaneously—expresses a human apo (a) is disclosed. In another embodiment, a dual transgenic mammal, a mouse, whose genome lacks the ability for endogenous ascorbate synthesis and—simultaneously—expresses a human apo B-100 is disclosed. In another embodiment, a transgenic mammal, a mouse, whose genome lacks the ability for endogenous ascorbate synthesis and—simultaneously—produces a human Lp(a) is disclosed. An animal model may be created by crossbreeding, gene insertion or other methods of molecular biology and/or genetic engineering.

In one embodiment, the novel dual transgenic mouse to be used as a model for cardio vascular disease (CVD) study. In another embodiment, the dual transgenic mice to be used as a model for treating CVD like diseases. In another embodiment, the dual transgenic mouse may be used as a model to test new and old drugs to treat diseases associated with Lp(a) synthesis and lack of vitamin C production.

In one embodiment, the dual transgenic mouse model may be used for testing effect of various drugs involved in ischemic heart disease, cardiovascular diseases, including coronary artery disease, cerebrovascular disease (stroke), renal vascular disease, peripheral vascular disease, aneurysms, thrombotic conditions, other forms of vascular disease, inflammatory conditions, as well as infectious diseases, neuroinflammatory and neurodegenerative diseases.

In one embodiment, a process for making a dual transgenic mammal which lacks the ability for endogenous ascorbate synthesis and—simultaneously—is capable of producing human apolipoprotein(a) or human apolipoprotein B or Lp(a) comprising mating a first mammal in which the ability for ascorbate synthesis has been genetically deleted with a second mammal which has a genome encoding human apo (a) or human apo B-100 or both of these apolipoproteins in such a manner that they combine in vivo in said transgenic mammal to produce the complete human lipoprotein(a) particle (Lp (a)).

In another embodiment, a method for determining whether a compound can treat atherosclerosis or an undesirable plasma lipid profile comprising: a) comparing the lipid profile or state of atherosclerosis in a first transgenic mammal fed a diet generally known to be atherogenic and treated with said compound, to the lipid profile or state of atherosclerosis in a second transgenic mammal fed the same atherogenic diet but not treated with said compound; and determining the potential therapeutic effect of said compound based upon comparative evaluation of the lipid profile or state of atherosclerosis in said first and second transgenic mammal; wherein said first and second transgenic mammal each being a transgenic mammal.

In one embodiment, a treatment method wherein the drug to treat the effect of high Lp(a) in the absence or in presence of micronutrients such as vitamin C is observed using transgenic mouse that does not produce vitamin C and produces human Lp(a).

The composition, method, and treatment disclosed herein may be implemented in any means for achieving various aspects, and may be executed in a form suitable for the mammal.

BRIEF DESCRIPTION OF DRAWINGS

Example embodiments are illustrated by way of example and not limitation in the Figures of the accompanying drawings, in which like references indicate similar elements and in which.

Figure 1:
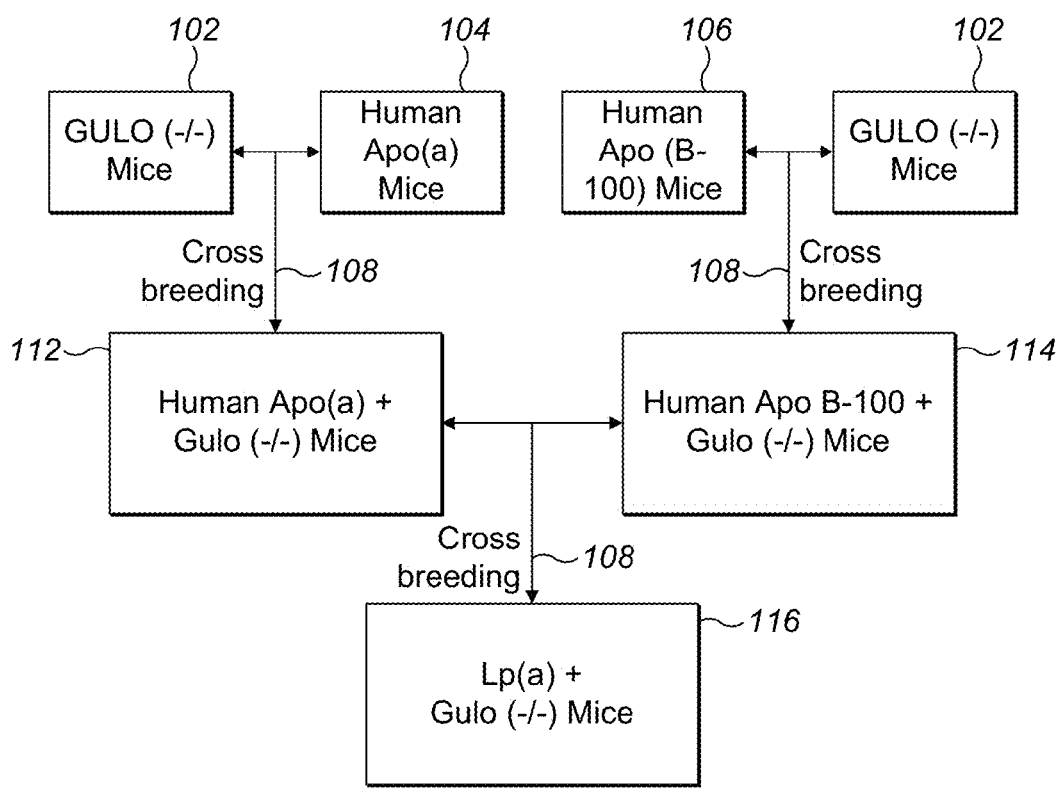
FIG. 1 shows the scheme used for creating the dual transgenic mouse.

Other features of the present embodiments will be apparent from the accompanying drawings and from the detailed description that follows.

DETAILED DESCRIPTION

The invention discloses novel dual transgenic mammal/ mouse, method of crossbreeding a dual transgenic mammal (may be a mouse or other animals) and the use of the dual transgenic mammal/mouse for assessing treatment method for cardiovascular and related diseases. The dual transgenic mouse expresses human apolipoprotein (a) and apolipoprotein B-100 genes and produces apolipoprotein (a) and apolipoprotein B-100 as well as complete human lipoprotein (a) particles in this mouse which, simultaneously, does not express L-gulonolactone oxidase (GULO −/−) and, consequently, does not produce vitamin C. This novel dual transgenic mouse is the ideal model for testing pharmaceutical compounds for treatment efficacy and usefulness for Lp(a) modulation with a variety of biological and/or pharmaceutical compounds, including but not limited to, nutrition, pharmaceutical drugs and treatment methods that affect human beings.

Although the present embodiments have been described with reference to specific example embodiments, it will be evident that various modifications and changes may be made to these embodiments without departing from the broader spirit and scope of the various embodiments.

Cross Breeding of Mammal/Mouse:

An animal model may be created by crossbreeding, gene insertion or other methods of molecular biology and/or genetic engineering. In an exemplary example crossbreeding of a knock mouse and a specific human expressing gene containing mouse is disclosed to create a dual transgenic mouse.

BALB/cBy-Gulo (−/−) Mouse:

The strain, BALB/cBy-Gulo$^{sfx}$/J was a spontaneous mutation, mapped to the Gulonolactone oxidase locus, the gene for vitamin C synthesis. The GULO (−/−) strain mouse (the first knockout strain of transgenic mouse) was generated from heterozygous (hemizygous) GULO (+/−) breeders obtained from The Jackson Laboratory (Table 1). The mouse was bred under vitamin C supplementation until an adequate number of homozygous GULO (−/−) breeders were obtained.

TABLE 1

| GULO (−/−) strain description: | |
|---|---|
| Allele Symbol | Gulo$^{sfx}$ |
| Allele Name | spontaneous fracture |
| Allele Type | Spontaneous |
| Strain of Origin | BALB/cBy-Rasa3 |
| Gene Symbol and Name | Gulo, gulonolactone (L−) oxidase |

TABLE 1-continued

GULO (−/−) strain description:

| | |
|---|---|
| Chromosome | 14 |
| Gene Common Name(s) | AU018375; BC028822; L-gulono-gamma-lactone oxidase; MGC:29968; MGC:37793; MGC:37880; cDNA sequence BC028822; expressed sequence AU018375; sfx; spontaneous fracture; |
| General Note | This spontaneous mutation appeared in a BALB/cBy-scat colony at The Jackson Laboratory. The scat and sfx mutations were separated from each other by backcrossing BALB/cBy-scat mouse to BALB/cBy mouse and observing F2 offspring for those that exhibited the sfx phenotype but not the scat phenotype. |
| Molecular Note | The mutation in the sfx mouse is a deletion that includes the entire Gulo gene. [MGI Ref ID J:95128] |

Maintenance of GULO (−/−) mouse: GULO (−/−) mouse are unable to synthesize their own vitamin C; therefore this nutrient needs to be present in the mouse diet. Vitamin C was provided in a double distilled drinking water containing 150 mg/L ascorbic acid (Sigma) and 0.01 mM EDTA (Sigma) to stabilize vitamin C from degradation by interaction with trace metals. The water also contained 10 g/L of sucrose in order to mask a taste offensive to mouse. Water was changed twice a week. In addition, these mouse received food fortified with 500 ppm L ascorbyl-polyphosphate, the standard veterinary feed source of stable vitamin C milled at Test Diet as Modified Custom Lab Diet #5A38.

Human Apo (a) Mouse:

The Human apo(a) mouse (second strain of transgenic mouse) was obtained from the Mutant Mouse Regional Resource Centers (MMRRC), supported by the NIH. The strain, FVB/N-Tg(LPA, LPAL2, PLG)1Hgc/Mmmh, was created using a 270 kb YAC that harbors human apo(a) and apo(a) like and plasminogen genes. The donor was Edward M. Rubin, M. D., Ph.D., Lawrence Berkeley National Laboratory. Founder mice were bred until sufficient number of apo(a)+ Gulo wildtype mice were obtained for crossbreeding. Genotyping for the transmission and presence of the transgene was performed at Transnetyx (Cordova, Tenn.) upon tail clip tissue and transgenic mutants confirmed positive for apo (a) in the genome selected for cross-breeding.

Human Apo B-100 Mouse:

The human apoB-100 mouse (fourth strain of transgenic mammal/mouse) was obtained from Taconic Farms, Inc. under academic research agreement. The strain, B6.5JL-Tg (APOB)1102Sgy N20+?, or apoB-100 mouse, was developed by MacRae F. Linton et. al. of the Gladstone Institute of Cardiovascular Disease by microinjecting the human apolipoprotein B100 gene into C57BL/6J×SJL zygotes. The resultant mouse was backcrossed to C57BL/6 for 4 generations (N4). Taconic received stock from Xenogen Biosciences in May 1996. The mouse was maintained by backcrossing hemizygous Apo (B-100) mouse with C57BL/6NTac inbred mouse. Hemizygous mouse were bred to obtain homozygous Apo (B-100) mouse. Genotyping for transmission and presence of the transgene Human Apo (B-100) in the genome was performed at Transnetyx upon tail clip tissue and transgenic mutants selected for cross-breeding.

Cross Breeding Steps Leading to Generating a Mouse Strain Producing Human Lp(a):

FIG. 1 shows the various steps used for crossbreeding several strains of mouse to obtain a dual transgenic mouse. The terms mouse and mice are used interchangeably and they all mean mouse in the instant specification. Crossbreeding (108) of human apo (a) mice (104) (the second strain of mammal)+GULO (−/−) (102) (a first knockout strain mammal) mice/mouse to produce a third strain of transgenic mammal/mouse that expresses the human apolipoprotein (a) gene (apo (a)+) and, simultaneously lacks the GULO gene (GULO−/−) (112) was performed. A GULO (−/−) (102) (a first knockout strain mammal) and human apo B-100 mouse represented as fourth strain of mammal (106) was crossbred (108) to produce a fifth strain of mouse that the fifth strain of mammal lacks the GULO gene (GULO−/−) and expresses the human apolipoprotein B-100 gene (apo (B-100)+) (114). Two transgenic founding strains were thus obtained for further crossbreeding:

Human apo(a)+ GULO (−/−) mouse—third strain of transgenic mouse

Human apo B-100+ GULO (−/−)mouse—fifth strain of transgenic mouse.

Crossbreeding (108) the Founding Strains for Obtaining Mouse Strain: Human Lp(a)+ GULO (−/−) (116):

Newly generated mouse breeders of human apo(a)+ GULO (−/−) mouse (112) and human apo B100+ GULO (−/−) (114) were subsequently crossed (108) with one another to generate the new mouse strain: human Lp(a)+GULO (−/−) mice (116) which had human apo(a)+ human ApoB-100+ GULO (−/−), named as "Rath M Human Lipoprotein(a); Gulo (−/−)" strain (116). The dual transgenic mouse embryo referred to as Rath M Human Lipoprotein(a); Gulo(−/−) has the Jackson Stock #912329, having been deposited in The Jackson Laboratory on Apr. 8, 2013.

Genotyping:

Genotyping for the GULO locus and its homozygosity was performed via Taqman FAM Probe Real Time-PCR at Transnetyx upon tail clip tissue derived DNA obtained using standard DNA isolation and PCR techniques. Transgene presence for human apo B-100 and human apo(a) were also conducted at Transnetyx.

Figure 2:
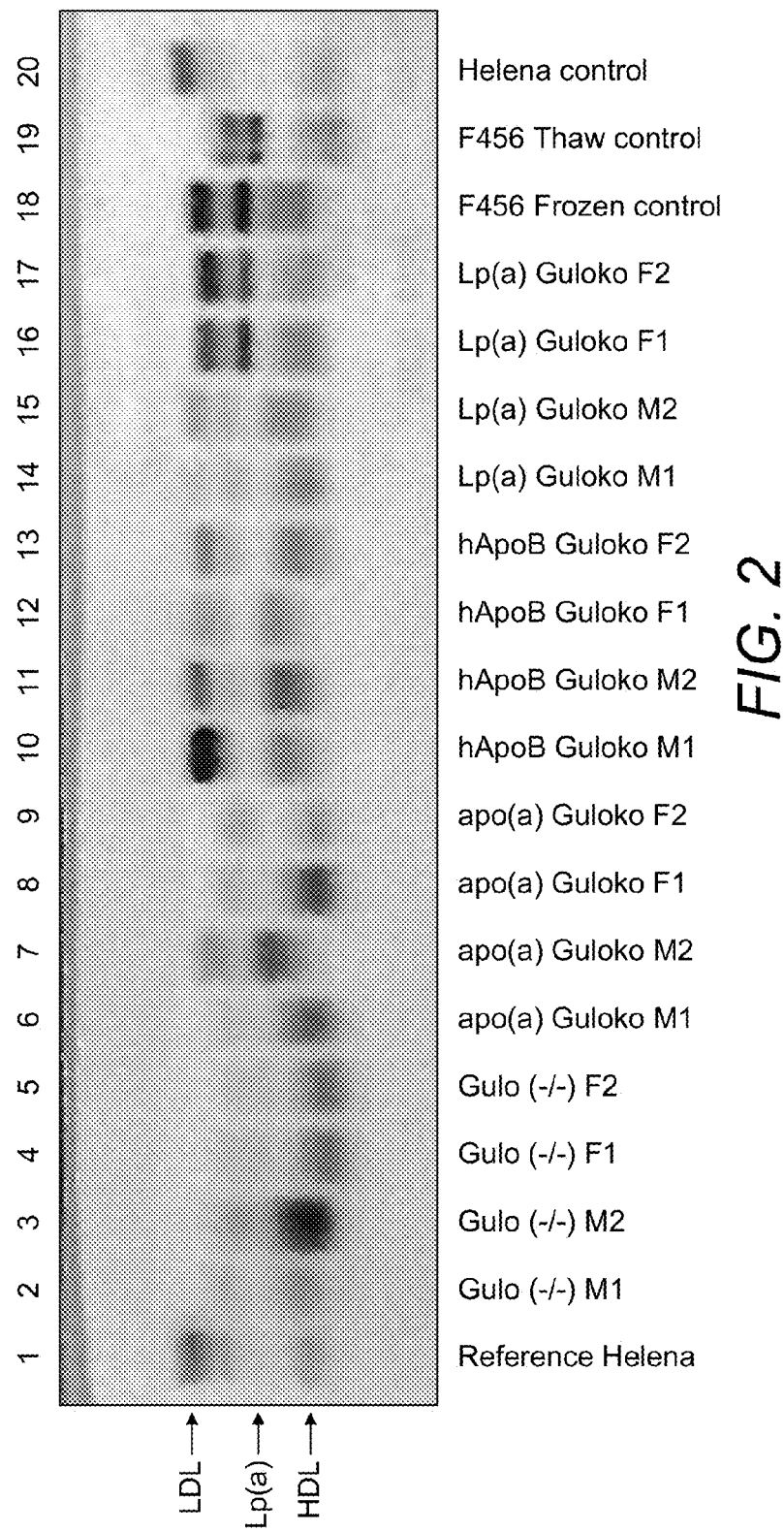
FIG. 2 shows the expression of disulfide linked human apo(a) and human apoB-100 as assembled Lp(a) with a lipid globule in male and female transgenic mouse with both human apo(a) and human apo B-100 genes, but not in male and female transgenic mouse without both genes.

Tail clips were obtained from mouse under anesthesia and then shipped to Transnetyx where the following probe sets were designed and used for Real-Time PCR detection of genomic DNA presence or absence (primers used are shown below in the Tables 2, 3 and 4. Litters were genotyped via tail clip Taqman PCR at Transnetyx and those positive for genomic transgenes apo(a) and apoB-100, as well as homozygous knockout mutation for the L-gulonolactone-oxidase gene, GULO (−/−), which indicates vitamin C synthesis defect, were selected and labeled as "Rath M Human Lipoprotein(a); Gulo (−/−)" founder mouse. In FIG. 2 we show that the disulfide linked lipoprotein (a) is formed in the dual transgenic mouse and shown as Lp(a) GULOKO F1, F2, M1 and M2. Similarly, the lack of Lp(a) in apo(a)+ mouse without human apoB-100 expression and apo B-100+mice without apo(a) expression is also shown.

TABLE 2

GULO testing:

| | |
|---|---|
| Gulo-1 KO Forward Primer: CTAGTGTAGTCTAGGTGATAAGGATCAACT | Seq 1 |
| Gulo-1 KO Reverse Primer: CAGCTCAGAGAGAGAATGAATCACA | Seq 2 |

TABLE 2-continued

GULO testing:

| | |
|---|---|
| Reporter 1:<br>CTGACATCCCTTAGGAGTTC | Seq 3 |
| Gulo-1 WT Forward Primer:<br>AGATGTGTTCCAGGCTGCAA | Seq 4 |
| Gulo-1 WT Reverse Primer:<br>CACACACTGCAGGGTGACA | Seq 5 |
| Reporter 1:<br>CTGCCTGGGTGTTATC | Seq 6 |

Genotype Results Interpretation: Gulo-1 KO+, Gulo-1 WT+=Hemizygous Vitamin C generating mouse. Gulo-1 KO−, Gulo-1 WT+=Homozygous wild type Vitamin C generating mouse. Gulo-1 KO+, Gulo-1 WT−=Homozygous Vitamin C defective mouse.

Mouse homozygous for the knockout, GULO(−/−) mouse was selected for cross-breeding.

TABLE 3

B: Human apo(a) testing

| | |
|---|---|
| HuLPA-1 Tg (Human apo(a) transgene)<br>Forward Primer:<br>CACTACATTTTGTGCCAGAGATGGA | Seq 7 |
| HuLPA-1 Tg Reverse Primer:<br>CCCTGTCCTGAGGCTCCTTA | Seq 8 |
| Reporter 1:<br>TCAGCAGCCCTCTTCC | Seq 9 |

Genotype Results Interpretation: +=Human apo(a) gene positive. −=Human apo(a) gene negative. Mouse positive for the transgene were selected for cross-breeding.

TABLE 4

Human apo B-100 testing primers

| | |
|---|---|
| ApoB Tg (Human ApoB100 Transgene)<br>Forward Primer:<br>AGGTTTAACTCCTCCTACCTCCAA | Seq 10 |
| ApoB Tg Reverse Primer:<br>TGAGGGAGAGGGTTCCATCTT | Seq 11 |
| Reporter 1:<br>ACCAGATAACAGGAAGATATG | Seq 12 |

Genotype Results Interpretation: +=Human apoB-100 gene positive. −=Human apoB-100 gene negative. Mouse positive for the transgene were selected for cross-breeding.

The genotype of the Lp(a); GULO (−/−) mouse is denoted as h apo(a)+; h apoB-100+; GULO(−/−). The mouse must continually be maintained on vitamin C supplementation as described above.

Confirming the transgene mouse generation at the level of protein: The presence of human apo(a) and human apo B-100 proteins in mouse sera was determined by ELISA in the serum drawn from the GULO (−/−) mouse, the apo(a)+ GULO(−/−) mouse, the apoB+ GULO (−/−) mouse, and the Lp(a)+ GULO (−/−) mouse.

TABLE 5

Lp(a); GULOKO mice and hApoB; GULOKO mice express human ApoB via AssayPro ApoB ELISA

| Sample name | ug/mL | ug/ml * 20000 | mg/dL |
|---|---|---|---|
| gko m1 | 0 | | |
| gko m2 | 0.001153 | | |
| gko f1 | 0.000374 | | |
| gko f2 | −0.00036 | | |
| Lp(a); gko m1 | 0.014717 | 294.3472224 | 29.4 mg/dL |
| Lp(a); gko m2 | 0.015867 | 317.346142 | 31.7 mg/dL |
| Lp(a); gko f1 | 0.041693 | 833.8570197 | 83.3 mg/dL |
| Lp(a); gko f2 | 0.041411 | 828.2183041 | 82.8 mg/dL |
| apo(a); gko m1 | 0.000185 | | |
| apo(a); gko m1 | −0.00018 | | |
| apo(a); gko f1 | −0.00054 | | |
| apo(a); gko f2 | −0.00018 | | |
| hApoB; gko m1 | 0.056842 | 1136.847637 | 114 mg/dL |
| hApoB; gko m2 | 0.020853 | 417.0655494 | 41.7 mg/dL |
| hApoB; gko f1 | 0.003275 | 65.5092541 | 6.6 mg/dL |
| hApoB; gko f2 | 0.017319 | 346.3860878 | 34.6 mg/dL |
| Serum diluted 1:20,000 | | | |

The apo(a) protein was present in serum of both male and female mouse before puberty. Male mouse after puberty have significantly or completely repressed apo(a) protein expression due to elevated testosterone levels. Apo(a) expression in male mouse may be restored via castration, continuous infusion of growth hormone via osmotic pump, or by biochemical modulation by dietary, chemical, or biological inducers.

Human apo B-100 protein expression: The presence of human apoB-100 protein in serum was determined by ELISA in a serum drawn from the GULO (−/−) mouse, the apo(a); GULO(−/−) mouse, the apoB; GULO (−/−) mouse, and the Lp(a); GULO (−/−) mouse.

Presence of apoB-100 protein in mouse serum was determined by using Assaypro (St. Charles, Mo.) AssayMax Human Apolipoprotein enzyme immunoassay which is human apoB-100 specific and does not cross-react with mouse apoB-100, and/or with any other of the apolipoproteins (Apo AI, ApoC, ApoE).

Human apoB-100 was detected in the sera of hApoB-100; GULO (−/−) mouse, hApoB-100; apo(a); GULO(−/−) mouse, but not apo(a); GULO (−/−) mouse or GULO (−/−) mouse (Table 5).

Serum apo(a) protein was present in apo(a) gene containing GULO (−/−) mouse, apo(a) and human ApoB-100 gene containing GULO (−/−) mouse, but not GULO (−/−) mouse without the transgene nor in GULO (−/−) mouse with only human apo B-100 (Table 6)). These results confirm expression and translation of the human transgene apo(a) to serum protein apo(a).

TABLE 6

Female and male apo(a) expression. Male mouse may have low expression because of high testosterone levels in blood.

| Sample names | mg/dL apo(a) | | Comments |
|---|---|---|---|
| GKO m1 | 0.66168 | (below detection limit) | This test does not cross react with plasminogen or LDL. |
| GKO m2 | 0 | (below detection limit) | |
| GKO f1 | −0.33084 | (below detection limit) | No apo(a) detected in background GULOKO mice. |

TABLE 6-continued

Female and male apo(a) expression. Male mouse may have low expression because of high testosterone levels in blood.

| Sample names | mg/dL apo(a) | | Comments |
|---|---|---|---|
| GKO f2 | −0.33084 | (below detection limit) | No apo(a) detected in hApoB; GULOKO mice. |
| Lp(a); gko m1 | 0.16542 | (below detection limit) | Extremely high apo(a) detected in apo(a); GULOKO female mice. |
| Lp(a); gko m2 | 0.16542 | (below detection limit) | No apo(a) detected in apo(a); GULOKO male mice. |
| Lp(a); gko f1 | 86.51466 | (#464) | Extremely high apo(a) detected in Lp(a); GULOKO female mice, either generation F1 or F2. |
| Lp(a); gko f2 | 79.4016 | (#110) | No apo(a) detected in Lp(a); GULOKO male mice, either F1 or F2. |
| apo(a); gko m1 | 0.33084 | (below detection limit) | |
| apo(a); gko m2 | −0.33084 | (below detection limit) | Sex steroid testosterone suppresses apo(a) production in these mice. |
| apo(a); gko f1 | 133.8248 | | Orchidectomy may have to be performed in order to express Lp(a). |
| apo(a); gko f2 | 156.1565 | | |
| hApoB; gko m1 | 0.16542 | (below detection limit) | (#110 - ApoB gene signal = 13.5, apo(a) gene signal = 3.7) |
| hApoB; gko m2 | 0 | (below detection limit) | (#464 - ApoB gene signal = 20.4, apo(a) gene signal = 8.5) |
| hApoB; gko f1 | −0.16542 | (below detection limit) | (#456 - ApoB gene signal = 18.8, apo(a) gene signal = 6.4) |
| hApob; gko f2 | 0.66168 | (below detection limit) | |

Human apo (a) protein expression: Presence of apo (a) protein in serum was determined by using the IBL International GmbH Lp(a) Enzyme immunoassay which is human apo (a) specific and does not cross-react with plasminogen or LDL. All known isoforms of apo(a) can be detected.

Human Lp(a) protein expression: The Lp(a) particles are composed of human apo(a) protein linked to human apo B-100 (the main protein of the LDL particle) by a disulfide bond.

SPIFE Cholesterol Profiling (FIG. 2): The presence of complete Lp(a) lipoprotein particles in the Lp(a)+ GULO (−/−) transgenic mouse serum was confirmed using the electrophoresis method with Helena (Beaumont, Tex.) SPIFE Cholesterol Profiling and Immunofixation electrophoresis (IFE).

The Lp(a)-cholesterol band runs at a specific migration distance in respect to LDL-cholesterol, and HDL-cholesterol, and it is found in human Lp(a)+; GULO(−/−) mouse sera, but not in the sera of GULO (−/−), human apo(a); GULO(−/−), or human apoB; GULO (−/−) mouse confirming that the presence of both human apoB-100 and human apo(a) are necessary to form complete Lp(a) particles in serum and that human apo(a) alone is insufficient to produce Lp(a) and it does not link to mouse LDL via disulfide bonds. In FIG. 2 the band closest to the top of the gel corresponds to LDL-cholesterol, and the band furthest from the top to HDL-cholesterol. The tight, middle bands located between the LDL and HDL bands which are present in lanes 16-18 represent the Lp(a)-cholesterol from three different female Lp(a); GULO(−/−) mice. These bands are missing from those GULO(−/−) mice not simultaneously expressing both human apo(a) and human apoB-100 transgenes. Lane 19 represents charge-mass shifts resulting from a 24 hour room temperature incubation of serum specimen #18, which indicates that a small shift in the particle migration may relate to lipoprotein oxidation.

Figure 3:
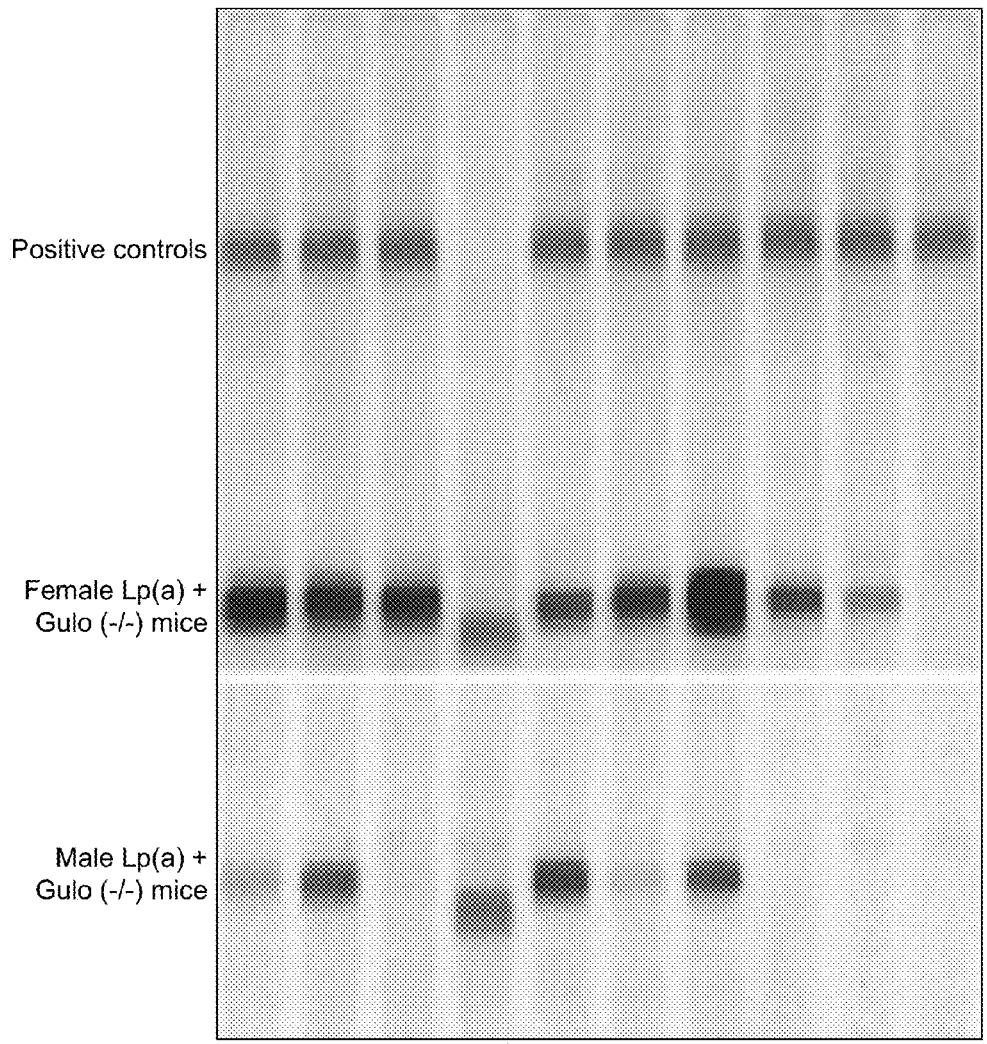
FIG. 3 shows the expression of human apo(a) protein in female and male mice.
Figure 4:
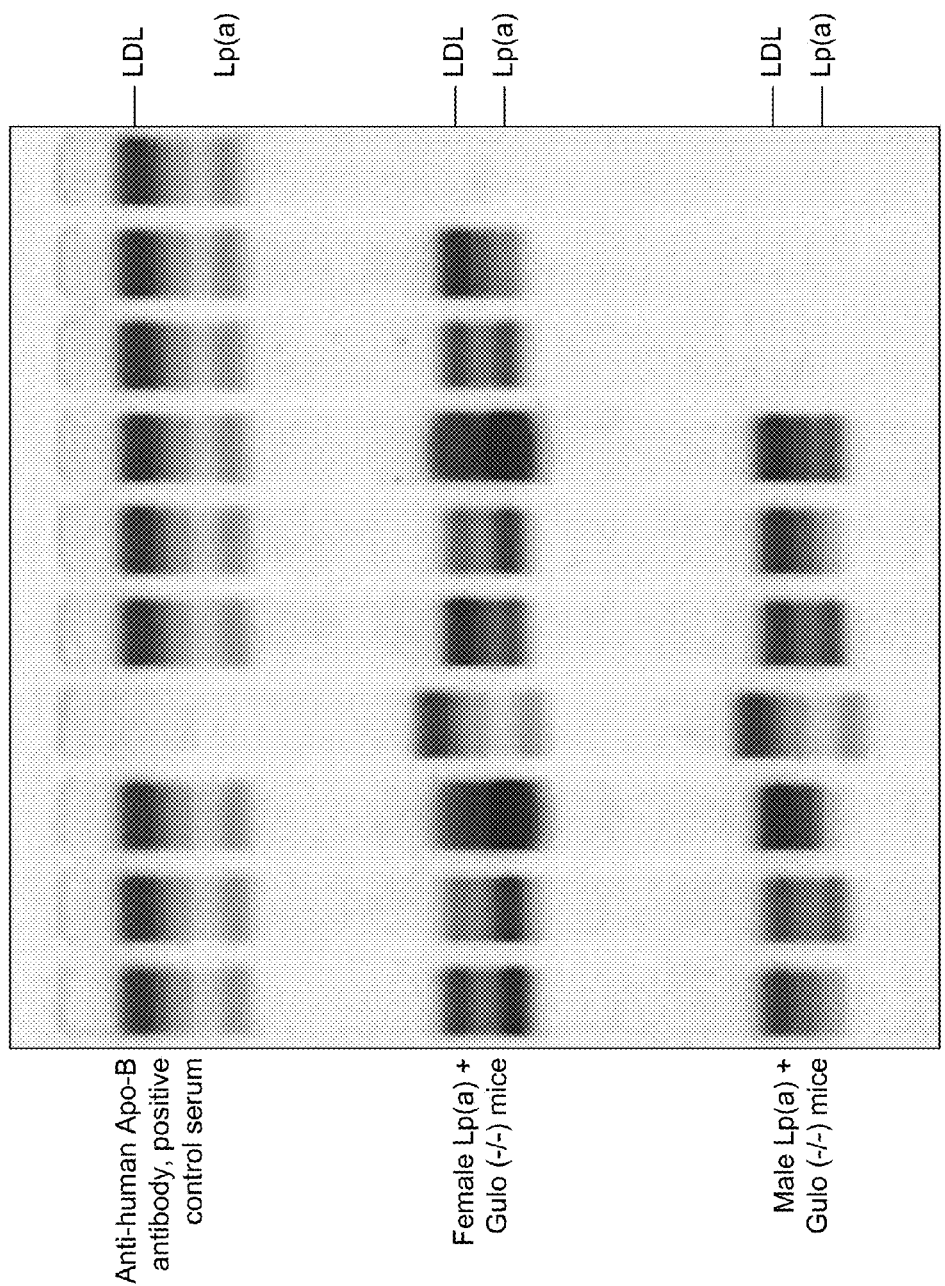
FIG. 4 shows the expression of human apo B-100 protein in female and male transgenic mouse in LDL particles and Lp(a) particles.

Immunofixation Electrophoresis (IFE) using the mouse sera was conducted on individual apo(a) (FIG. 3) containing particles and human apoB-100 containing particles (FIG. 4) as well, using human specific apo(a) and apoB-100 antibodies at Health Diagnostic Laboratory, Inc. (Richmond, Va.). The bands represent apo(a) and apoB-100 protein respectively in transgenic mouse and visualization of the same in serum derived from female and male mouse.

Figure 5:
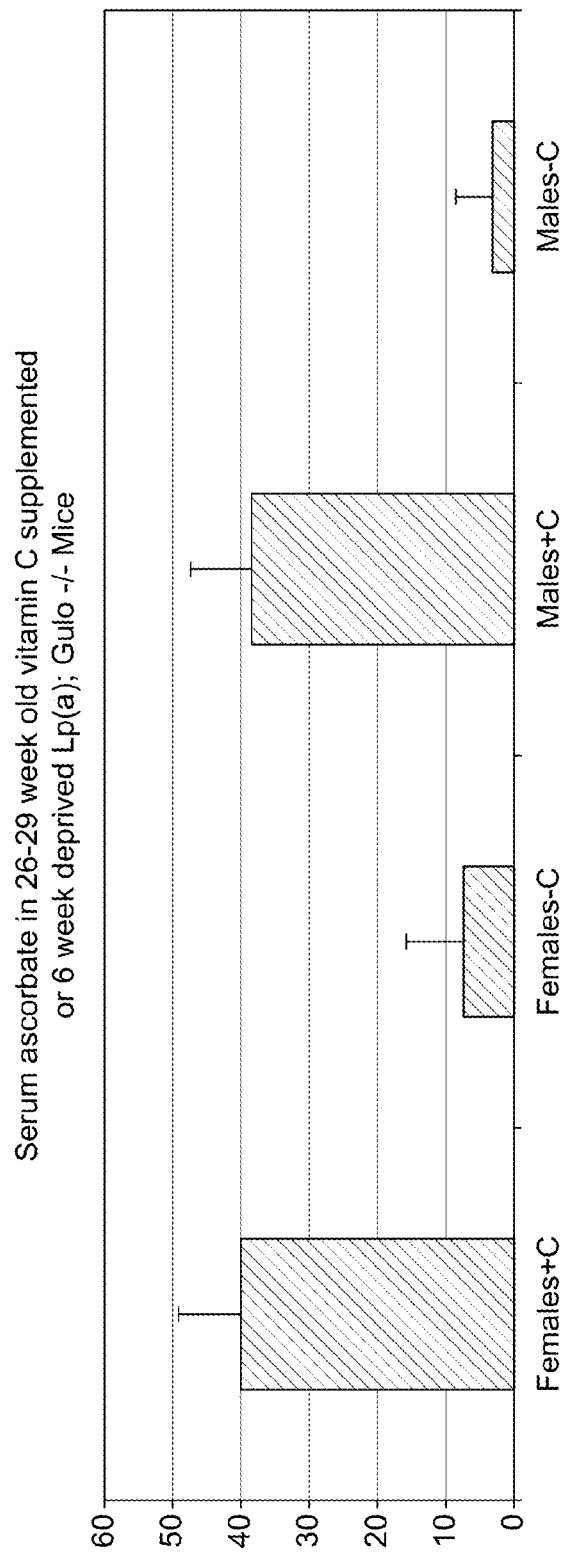
FIG. 5 shows the serum ascorbate level in transgenic female and male mouse (26-29 weeks old) supplemented with Vitamin C or deprived of Vitamin C in micromoles/liter (uM).

Confirming a lack of vitamin C production in the transgenic mouse strains: Serum level of ascorbate (vitamin C) in both GULO(−/−) mouse and a newly generated strain of Lp(a)+GULO (−/−) depends on its dietary supplementation. Mouse kept on vitamin C deficient diet has a gradually diminishing serum concentration of vitamin C until it reaches zero or the mouse dies. Serum levels of vitamin C were obtained using the Biovision (Mountain View, Calif.) Ferric Reducing Ascorbate Assay (FRASC) Kit (FIG. 5).

Lipoprotein-cholesterol, Apo(a) particle, and ApoB-100 particle Modulation (FIG. 6, FIG. 7, and FIG. 8): The analysis was conducted on mouse sera from the Lpa+ Gulo (−/−) mouse supplemented with either 30 mg/L, 60 mg/L or 150 mg/L of ascorbic acid provided in drinking water in addition to 500 ppm vitamin C provided in food (full supplementation). It was observed that the whole spectrum of lipoprotein cholesterols and/or lipoprotein particles could be modulated by dietary ascorbate alone. These data give additional particle number data and in conjunction with the lipoprotein cholesterol load data provided comprehensive confirmation of the presence of apo(a) protein, human apoB-100 protein, and disulfide linked Lp(a) in these mouse sera.

Figure 6:
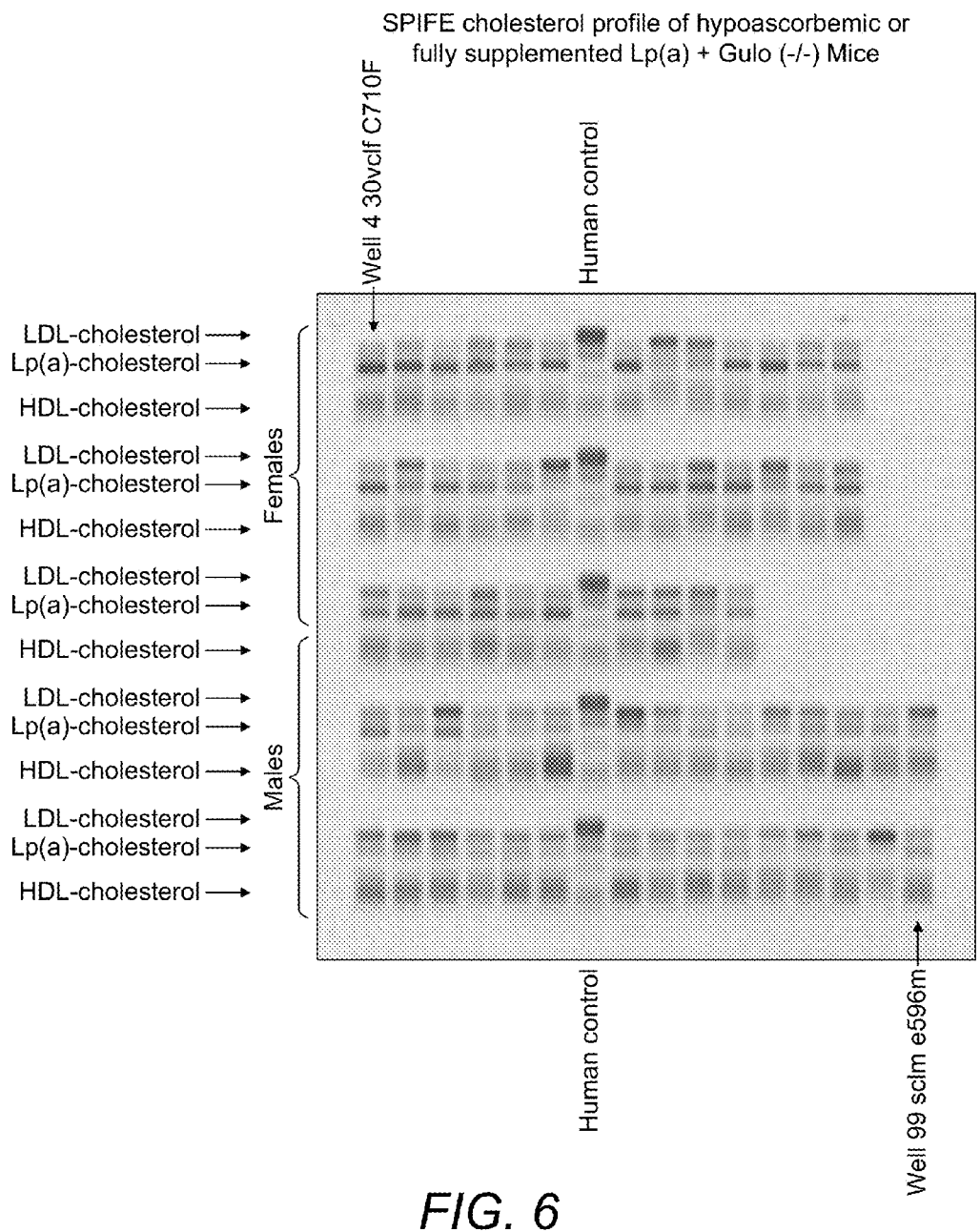
FIG. 6 shows Serum Protein Immunofixation Electrophoresis (SPIFE) cholesterol profile of hypoascorbemic or fully ascorbate-supplemented Lp(a)+GULO (−/−) mouse.
Figure 7:
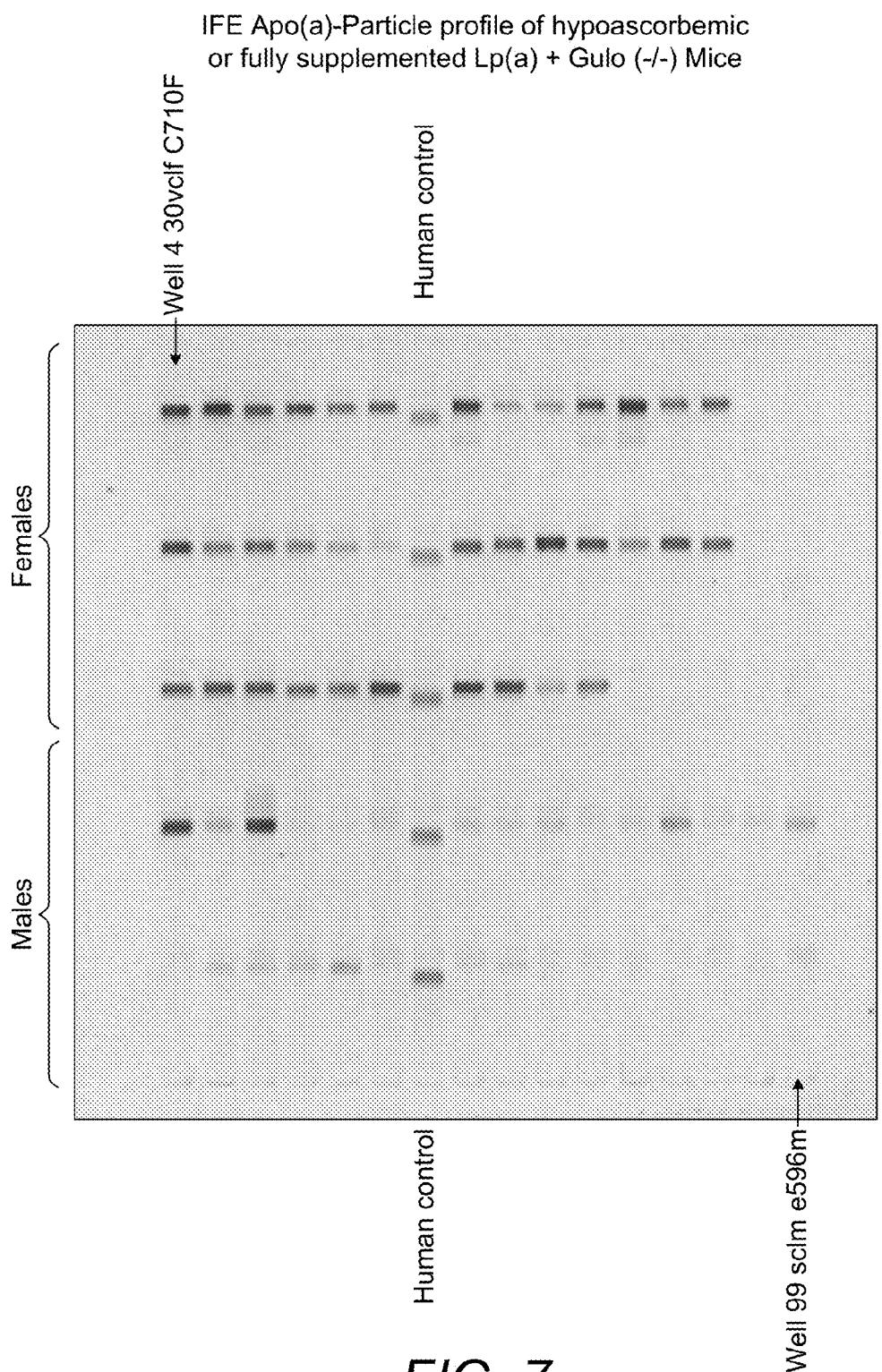
FIG. 7 shows Immunofixation Electrophoresis (IFE) apo (a)-particle profile of hypoascorbemic or fully ascorbate-supplemented Lp(a)+GULO (−/−) mouse.
Figure 8:
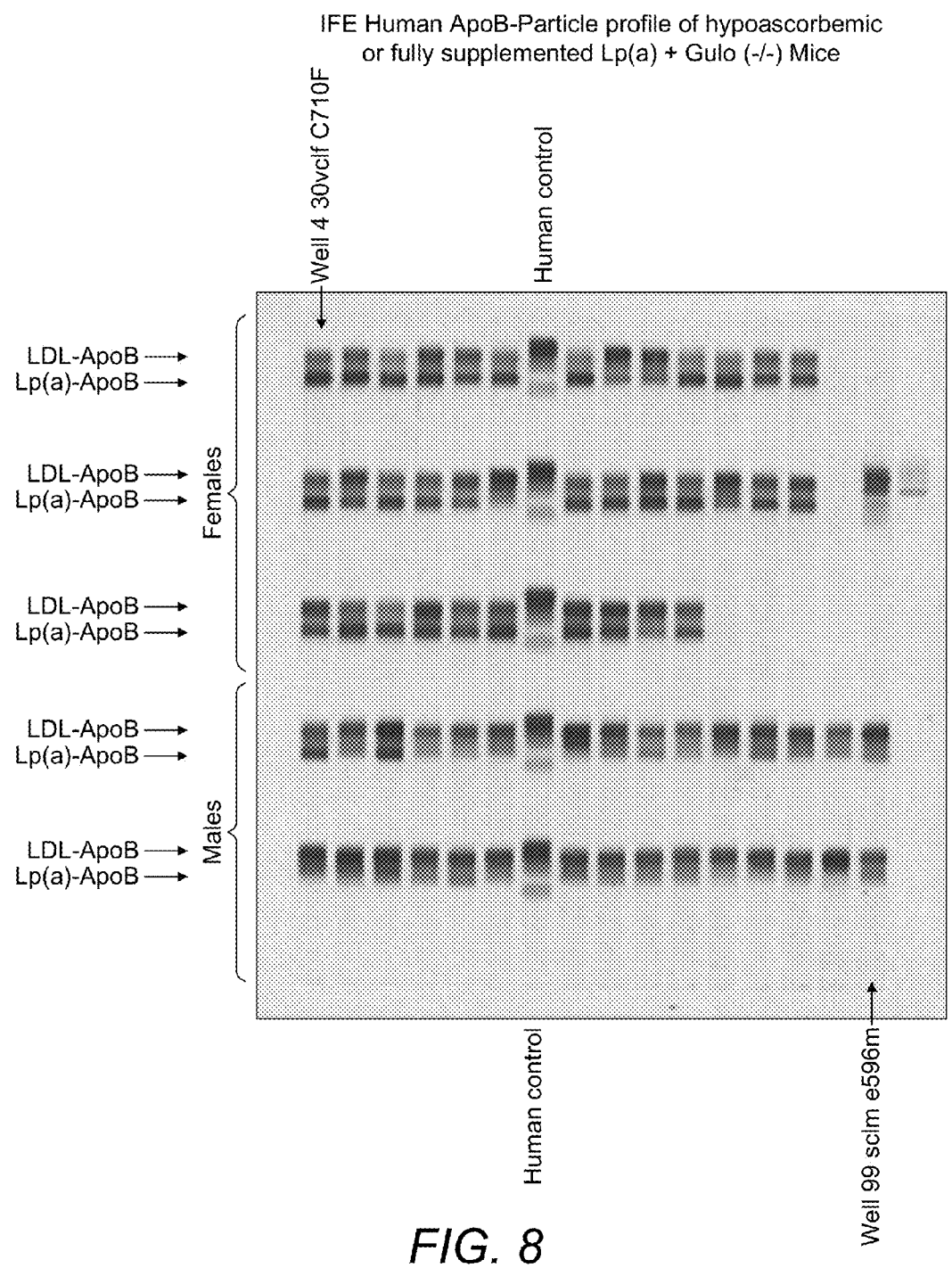
FIG. 8 shows IFE Human Apo B-Particle profile of hypoascorbemic or fully ascorbate-supplemented Lp(a)+GULO (−/−) mouse.

Sample order in FIGS. 6-8 correspond to the following key, with 30vc referring to 30 mg/L Vitamin C group, 60vc referring to 60 mg/L Vitamin C group, and sc referring to fully supplemented (150 mg/L Vitamin C+500 ppm Vitamin C in food) control group. The first three wells of each row were not used.

TABLE 7

Sample list for the wells in FIG. 6, 7 and 8.

| Well # | Group | Sample ID |
|---|---|---|
| 4 | 30vc1f | e710f |
| 5 | 30vc2f | e689f |
| 6 | 30vc2f | e598f |
| 7 | 30vc2f | e704f |
| 8 | 30vc2f | e723f |
| 9 | 30vc2f | e717f |
| 10 | human control | |
| 11 | 30vc1f | fell off 1 |
| 12 | 30vc1f | e762f |
| 13 | 30vc1f | e759f |
| 14 | 30vc1f | e699f |
| 15 | 30vc1f | e706f |
| 16 | 30vc1f | fell off 2 |
| 17 | 60vc2f | e773f |
| 24 | 60vc2f | ea315f |
| 25 | 60vc2f | e771f |
| 26 | 60vc2f | e694f |
| 27 | 60vc2f | e761f |
| 28 | 60vc2f | e768f |
| 29 | 60vc1f | e776f |
| 30 | human control | |

TABLE 7-continued

Sample list for the wells in FIG. 6, 7 and 8.

| Well # | Group | Sample ID |
|---|---|---|
| 31 | 60vc1f | e777f |
| 32 | 60vc1f | e780f |
| 33 | 60vc1f | fell off |
| 34 | 60vc1f | e733f |
| 35 | 60vc1f | e784f |
| 36 | sc2f | e741f |
| 37 | sc2f | e814f |
| 44 | sc2f | fell off 2 |
| 45 | sc2f | fell off 1 |
| 46 | sc2f | e781f |
| 47 | sc1f | e732f |
| 48 | sc1f | e730f |
| 49 | sc1f | e739f |
| 50 | human control | |
| 51 | sc1f | e731f |
| 52 | sc1f | e812f |
| 53 | sc1f | e832f |
| 54 | sc2f | e778f |
| 64 | 30vc2m | e697m |
| 65 | 30vc2m | e698m |
| 66 | 30vc2m | e770m |
| 67 | 30vc2m | fell off |
| 68 | 30vc2m | e695m |
| 69 | 30vc1m | e683m |
| 70 | human control | |
| 71 | 30vc1m | e684m |
| 72 | 30vc1m | fell off |
| 73 | 30vc1m | e693m |
| 74 | 30vc1m | e727m |
| 75 | 60vc2m | e782m |
| 76 | 60vc2m | fell off 2 |
| 77 | 60vc2m | fell off 1 |
| 78 | 60vc2m | e809m |

TABLE 7-continued

Sample list for the wells in FIG. 6, 7 and 8.

| Well # | Group | Sample ID |
|---|---|---|
| 79 | 60vc2m | e738m |
| 84 | 60vc1m | e811m |
| 85 | 60vc1m | e736m |
| 86 | 60vc1m | fell off |
| 87 | 60vc1m | e734m |
| 88 | 60vc1m | e740m |
| 89 | sc2m | fell off 2 |
| 90 | human control | |
| 91 | sc2m | e724m |
| 92 | sc2m | e605m |
| 93 | sc2m | e702m |
| 94 | sc2m | fell off 1 |
| 95 | sc1m | e705m |
| 96 | sc1m | e718m |
| 97 | sc1m | e701m |
| 98 | sc1m | e703m |
| 99 | sc1m | e596m |

INDUSTRIAL APPLICATION

Crossbreeding a dual transgenic mouse to produce a human Lp(a) and not produce vitamin C due to lack of GULO (GULO−/−) gene using transgenic mouse having a first knockout strain, a second strain to make a third strain and using the first knockout strain and fourth strain to make a fifth strain, using the third strain and the fifth strain to make a dual transgenic mouse. Treating the dual transgenic mouse with a Lp(a)-modulating compounds in order to identify preventive and/or therapeutic approaches for a human Lp(a)-related diseases. The human Lp(a)-related disease is cardiovascular, inflammatory, infectious or degenerative in nature.

What is claimed is:

1. A transgenic mouse whose genome comprises a disruption of a gulonolactone oxidase gene (GULO) and whose genome also comprises a human apolipoprotein (a) (apo(a)) gene, wherein said transgenic mice produces no Vitamin C and produces human apo(a).

2. A transgenic mouse whose genome comprises a disruption of a GULO gene and whose genome also comprises a human apolipoprotein B-100 (apo(B-100)) gene, wherein said mouse produces no Vitamin C and produces human apo B-100.

3. A transgenic mouse whose genome comprises a disruption of a GULO gene and also comprises a human apo(a) gene and human apo(B-100), and the transgenic mouse produces no Vitamin C and expresses both the human apo(a) gene and the human apo(B-100) gene, wherein the transgenic mouse produces human lipoprotein (a) (Lp(a)).

4. A method, comprising,
crossbreeding a transgenic mouse whose genome comprises a disruption of a gulonolactone oxidase gene (GULO) and whose genome also comprises a human apo(a) gene, and wherein said transgenic mouse produces no Vitamin C and produces human apo(a) with a transgenic mouse whose genome comprises a disruption of a gulonolactone oxidase gene (GULO) and whose genome also comprises a human apo(B-100) gene, wherein said mouse produces no Vitamin C and produces human apo(B-100) to produce a transgenic mouse whose genome comprises a disruption of GULO gene and whose genome also comprises a human apo(a) gene and a human apo(B-100) gene, wherein said transgenic mouse produces no Vitamin C, and produces human apo(a) and human apo(B-100), and wherein said transgenic mouse further produces lipoprotein a (Lp(a)).

5. A method comprising,
crossbreeding a transgenic mouse whose genome comprises a disruption of a GULO, wherein said transgenic mouse produces no Vitamin C with a transgenic mouse whose genome comprises a human apo(a) gene, wherein said transgenic mouse produces human apo(a) to produce a transgenic mouse whose genome comprises a disruption of a GULO gene and whose genome also comprises a human apo(a) gene, wherein said transgenic mouse produces no Vitamin C, and produces human apo(a).

6. A method comprising,
crossbreeding a transgenic mouse whose genome comprises a disruption of a GULO, wherein said transgenic mouse produces no Vitamin C with a transgenic mouse whose genome comprises a human apo(B-100) gene, wherein said transgenic mouse produces human apo(B-100) to produce a transgenic mouse whose genome comprises a disruption of a GULO gene and whose genome also comprises a human apo(B-100) gene, wherein said transgenic mouse produces no Vitamin C, and produces human apo(B-100).

7. The method of claim 4, 5 or 6, further comprising testing the transgenic mouse for the presence of human apo(a) and human apo(B-100) and lack of GULO gene using specific sequence of primer.

8. The method of claim 7, wherein the specific sequences of primer are SEQ ID NO: 1 to SEQ ID NO: 12.

9. A method comprising,
a) administering a pharmaceutical drug transgenic mouse whose genome comprises a disruption of a GULO gene and also comprises a human apo(a) gene and human apo(B-100), and the transgenic mouse produces no Vitamin C and expresses both the human apo(a) gene and the human apo(B-100) gene, wherein the transgenic mouse produces human Lp(a); and
b) determining the effect of said drug on Lp(a) synthesis and/or Lp(a) blood levels and/or Lp(a) deposition inside the vascular wall in said transgenic mouse producing Lp(a) as compared to a control transgenic mouse producing Lp(a) not administered said pharmaceutical drug,
wherein a drug that reduces Lp(a) synthesis and/or reduces Lp(a) blood levels and/or Lp(a) deposition inside the vascular wall of said administered transgenic mouse of step b) as compared to said transgenic mouse not administered of step b) indicates a potential use of said drug to treat a cardiovascular disease.

* * * * *

SEQUENCE LISTING

<160> NUMBER OF SEQ ID NOS: 12

<210> SEQ ID NO 1
<211> LENGTH: 30
<212> TYPE: DNA
<213> ORGANISM: Mouse

<400> SEQUENCE: 1
ctagtgtagt ctaggtgata aggatcaact                                    30

<210> SEQ ID NO 2
<211> LENGTH: 25
<212> TYPE: DNA
<213> ORGANISM: Mouse

<400> SEQUENCE: 2
cagctcagag agagaatgaa tcaca                                         25

<210> SEQ ID NO 3
<211> LENGTH: 20
<212> TYPE: DNA
<213> ORGANISM: Mouse

<400> SEQUENCE: 3
ctgacatccc ttaggagttc                                               20

<210> SEQ ID NO 4
<211> LENGTH: 20

```
<212> TYPE: DNA
<213> ORGANISM: Mouse

<400> SEQUENCE: 4
agatgtgttc caggctgcaa                                          20

<210> SEQ ID NO 5
<211> LENGTH: 19
<212> TYPE: DNA
<213> ORGANISM: Mouse

<400> SEQUENCE: 5
cacacactgc agggtgaca                                           19

<210> SEQ ID NO 6
<211> LENGTH: 16
<212> TYPE: DNA
<213> ORGANISM: Mouse

<400> SEQUENCE: 6
ctgcctgggt gttatc                                              16

<210> SEQ ID NO 7
<211> LENGTH: 25
<212> TYPE: DNA
<213> ORGANISM: Human

<400> SEQUENCE: 7
cactacattt tgtgccagag atgga                                    25

<210> SEQ ID NO 8
<211> LENGTH: 20
<212> TYPE: DNA
<213> ORGANISM: Human

<400> SEQUENCE: 8
ccctgtcctg aggctcctta                                          20

<210> SEQ ID NO 9
<211> LENGTH: 16
<212> TYPE: DNA
<213> ORGANISM: Human

<400> SEQUENCE: 9
tcagcagccc tcttcc                                              16

<210> SEQ ID NO 10
<211> LENGTH: 24
<212> TYPE: DNA
<213> ORGANISM: Human

<400> SEQUENCE: 10
aggtttaact cctcctacct ccaa                                     24

<210> SEQ ID NO 11
<211> LENGTH: 21
<212> TYPE: DNA
<213> ORGANISM: Human

<400> SEQUENCE: 11
tgagggagag ggttccatct t                                        21

<210> SEQ ID NO 12
```

```
<211> LENGTH: 21
<212> TYPE: DNA
<213> ORGANISM: Human

<400> SEQUENCE: 12
accagataac aggaagatat g                                             21
```